United States Patent [19]
Wein

[11] Patent Number: 5,278,402
[45] Date of Patent: Jan. 11, 1994

[54] REAL-SCENE DISPERSION SENSOR DETECTING TWO WAVELENGTHS AND DETERMINING TIME DELAY

[75] Inventor: Steven J. Wein, Sudbury, Mass.

[73] Assignee: Litton Systems, Lexington, Mass.

[21] Appl. No.: 73,953

[22] Filed: Jun. 9, 1993

[51] Int. Cl.⁵ .............................. G01J 1/20; G01J 3/50
[52] U.S. Cl. .................... 250/201.9; 250/226
[58] Field of Search ............... 250/201.9, 226, 237 R, 201.1; 356/121, 128

[56] References Cited

U.S. PATENT DOCUMENTS

| | | | |
|---|---|---|---|
| 3,033,924 | 5/1962 | Ainsworth, Jr. | 178/6.8 |
| 3,869,705 | 3/1975 | Woywood et al. | 358/5 |
| 3,952,151 | 4/1976 | Jenkin | 178/6.8 |
| 4,152,725 | 5/1979 | Beckmann | 358/109 |
| 4,304,491 | 12/1981 | Kraushaar et al. | 356/326 |
| 4,391,522 | 7/1983 | Schmid et al. | 356/326 |
| 4,519,707 | 5/1985 | Kuffer | 356/326 |
| 4,620,790 | 11/1986 | Hufnagel | 356/124 |
| 4,630,111 | 12/1986 | Blain et al. | 358/109 |
| 4,695,964 | 9/1987 | Seto et al. | 364/518 |
| 4,953,972 | 9/1990 | Zuk | 356/4 |
| 5,093,563 | 3/1992 | Small et al. | 250/201.9 |
| 5,165,063 | 11/1992 | Strater et al. | 250/201.8 |
| 5,173,748 | 12/1992 | Bilhorn | 250/201.9 |
| 5,229,592 | 7/1993 | Horwitz et al. | 250/201.9 |

*Primary Examiner*—Michael Messinger
*Attorney, Agent, or Firm*—Michael H. Wallach

[57] ABSTRACT

An optical dispersion sensor for sensing optical dispersion introduced by the atmosphere in near real-time and an optical system using the dispersion sensor to compensate for atmospheric dispersion are described. The input signal to the dispersion sensor is the image of the scene being viewed by a scanning optical system. The image of the scene is passed through an aperture near the image plane of the optical system and then onto at least two individual light detecting systems. One of the detecting systems is adapted to detect light of a first wavelength band. The other detecting system detects light of a second wavelength band. The sensor computes the relative time delay between the signals derived from the two detecting systems. The time delay indicates the spectral dispersion introduced by the atmosphere. In an optical system, a control circuit adjusts a variable dispersive element contained within the optical system to compensate for the atmospheric dispersion by driving the relative time delay between signals towards zero.

42 Claims, 7 Drawing Sheets

REAL-SCENE DISPERSION SENSOR DETECTING TWO WAVELENGTHS AND DETERMINING TIME DELAY

BACKGROUND OF THE INVENTION

In many optical systems, it is necessary to gather light from very distant scenes at oblique viewing angles through the atmosphere. These systems include ground-based telescopes which view astronomical objects as well as airborne or space-borne surveillance systems which monitor the ground.

As the light travels through the atmosphere, it is spectrally dispersed. This spectral dispersion can have negative effects on the operation of the optical system. It is desirable to sense the amount of dispersion introduced by the atmosphere so that the dispersion, and thus its deleterious effects on the optical system, can be compensated.

SUMMARY OF THE INVENTION

The present invention relates to an optical dispersion sensor and an optical system for compensating for atmospheric spectral dispersive effects. The present invention also relates to a method of sensing optical dispersion and a method of compensating for atmospheric dispersive effects in an optical system.

In accordance with the invention, an aperture is placed near the image plane of an optical system. The image of the scene is scanned across the aperture. The aperture can be an approximately circular pinhole or a single slit or a pair of approximately orthogonal slits depending upon the scan direction relative to direction of the atmospheric dispersion. (The atmospheric dispersion occurs in a plane perpendicular to the horizon.) The pair of orthogonal slits corresponds to the case of an arbitrary scan direction. The dispersion sensor comprising two light detecting systems receives light from the aperture. The first light detecting system detects light of a first wavelength band and generates signals corresponding to that detected light. The second light detecting system detects light of a second wavelength band and generates signals corresponding to that detected light. A processing circuit receives the signals generated by the first and second light detecting systems. Because of the spectral dispersion introduced by the atmosphere, the signals are highly correlated but exhibit a relative time delay. That is, one of the light detecting systems will indicate detection of a specific region of the scene before the other light detecting system will indicate detection of the same region. The processing circuit senses the time delay between the detections of the region. This time delay is a direct measure of the spectral dispersion introduced by the atmosphere.

The dispersion sensor can be part of a larger optical system having correction or compensation for atmospheric spectral dispersion. A dispersion compensating element receives light from the scene and introduces spectral dispersion into the light. The amount of spectral dispersion introduced is adjustable. A control circuit adjusts the spectral dispersion in order to reduce the relative time delay sensed by the processing circuit to approximately zero. When this is accomplished, the spectral dispersion introduced by the atmosphere is substantially compensated such that there is virtually no net dispersion.

In one embodiment of the dispersion sensor, light from the image plane aperture is dispersed by a prism. The light is spectrally separated and the light from one spectral band is focused onto an optical detector and light from another spectral band is focused onto another detector. One of the detectors senses light of the first wavelength band, and the other detects light of the second wavelength band. In another embodiment, a dichroic beam splitter takes the place of the prism. The beam splitter directs some light through a narrow spectral band filter to a first detector. The filter passes only light of the first wavelength band. The remainder of the light is directed to a second detector through another filter which passes only light of the second wavelength band.

In one embodiment, a spectrometer receives the light from the aperture. The spectrometer spectrally disperses the signals and directs the light of the two different wavelengths onto the two separate detectors In another embodiment, a partially transmitting mirror receives light from the aperture. Some of the light is directed to the first light detecting system; the remaining light is directed to the second light detecting system. The first light detecting system has a filter which transmits only light of the first wavelength band onto an optical detector. The second light detecting system has a filter which transmits only light of the second wavelength band onto another optical detector.

The aperture can be a pinhole, a single slit, or a pair of orthogonal slits. When the aperture is a pinhole, the dispersion sensor senses atmospheric dispersion when the scan direction of the sensor is the same as the dispersion direction of the atmosphere. When the aperture is a single slit and the scan direction is known, the scan direction can be in any direction relative to the dispersion direction of the atmosphere; except a scan direction which is near orthogonal to the dispersion direction. When the scan direction is orthogonal to the dispersion direction, the dispersed footprints of the slit do not scan over the same path on the ground and a correlated signal is not obtained. When the aperture is a pair of orthogonal slits, the dispersion sensor measures dispersion in an arbitrary scan direction with respect to the atmospheric dispersion direction. In addition, the scan direction need not be known with a pair of orthogonal slits since each slit determines a vector component of the dispersion and thus the dispersion magnitude and orientation can be deduced from the individual time delays.

In the orthogonal-slit embodiment, light from the scene is first split by a partially transmitting mirror. Some of the light is directed to one of the slits, while the remaining light is directed to a slit orthogonal to the first slit. Each of the beams leaving the slits is then applied to its own first and second light detecting systems to determine the amount of atmospheric spectral dispersion.

In another embodiment, the two orthogonal slits are separated in the image field; thus, the center of each slit is looking through slightly different paths through the atmosphere. In this embodiment, the light from the scene does not need to be split before it reaches the slits.

The light detecting systems can be implemented on a single two-dimensional array of CCD pixels. The light from the aperture is spectrally dispersed by a prism or one of the other methods mentioned above and is then re-imaged onto the two-dimensional array of pixels. The pixel array is oriented such that each row of pixels corresponds to a single wavelength band in the spectrum. Therefore, the light detecting system for the first wavelength is simply a row of pixels in the array. The light detecting system for the second wavelength is another row of pixels in the array.

Alternatively, as mentioned above, each of the detecting systems can comprise a simple photodetector. In those embodiments, the light from the aperture is again spectrally dispersed. However, rather than imaging the light onto an array of pixels, it is directed at a pair of photodetectors. One of the photodetectors is oriented to receive light of the first wavelength, while the other receives light of the second wavelength.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
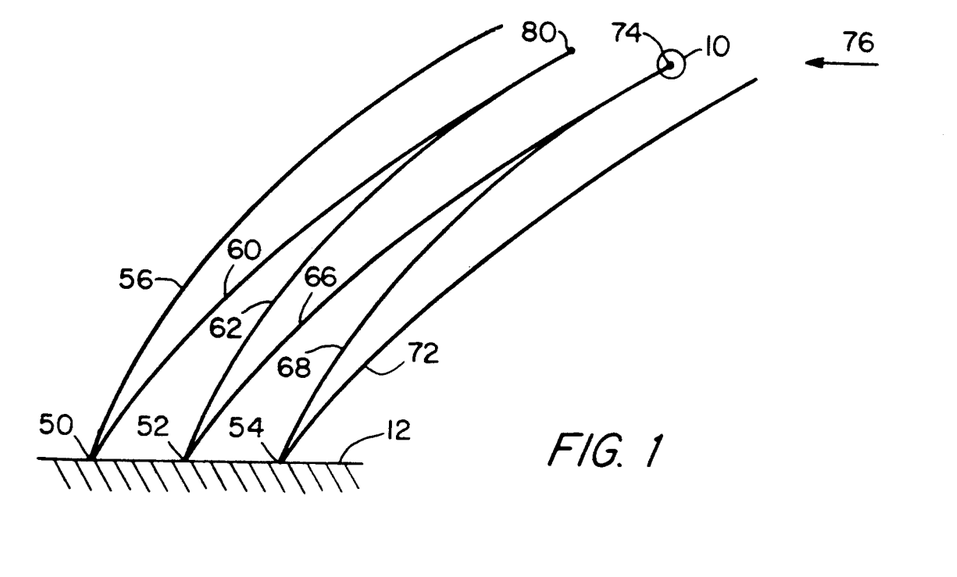
FIG. 1 illustrates dispersion of light by the atmosphere and the operation of the dispersion sensor of the present invention.

FIG. 1 schematically illustrates the atmospheric dispersion of light and the operation of the dispersion sensor 10 of the present invention. FIG. 1 depicts three points on the ground 50, 52 and 54 and the dispersion of light emanating from them. The light is dispersed as it travels from the ground 12 up through the atmosphere.

Two lines are shown emanating from each point on the ground. Each line represents a color in the spectrum of light from each point. For illustration purposes, it will be assumed that the red and blue lines are shown for each point. It should be noted that throughout this application red light and blue light are chosen for illustration purposes only. It is not required that these colors be used. For point 50 the blue and red lines are labelled 56 and 60, respectively. For point 52 they are labelled 62 and 66, respectively; for point 54 they are labelled 68 and 72, respectively.

White light from the ground 12 is collected by the dispersion sensor 10. In FIG. 1, the dispersion sensor 10 is shown located at point 74 above the ground. At this point, the red light 66 from point 52 intersects the blue light 68 from point 54. Thus, because of atmospheric dispersion, the dispersion sensor 10 sees a different point on the ground for each wavelength. The dispersion sensor collects a whole spectrum of visible light, each wavelength coming from a different point on the ground. For example, although not shown in FIG. 1, the dispersion sensor 10 at point 74 also sees the yellow light from a point located on the ground somewhere between points 52 and 54.

The dispersion sensor 10 scans the scene in order to sense the atmospheric dispersion. In FIG. 1, it is assumed that the dispersion sensor 10 moves or scans the ground horizontally in the direction indicated by arrow 76. As the sensor 10 scans the ground, it receives a time-varying white light signal from the ground 12. This white light is not the combination of colored light from single points on the ground. Rather, at each instant in time, the signal is made up of the colored components from several different points. Since a real scene can be considered to be composed of an infinite number of individual points, the dispersion sensor 10 operates by sensing the relative time delay between sensing the same points on the ground but in the different spectral bands.

The dispersion sensor 10 has a first light detecting system (detector) which detects light of a first wavelength band. In this illustration, the first detecting system detects red light. It also has a second light detecting system (detector) which detects blue light. As the sensor 10 moves or scans a scene, each of the detectors generates an electronic signal indicative of the intensity of the light sensed. The red detector outputs a signal indicative of the intensity of red light in the scene, while the blue detector outputs a signal indicative of the intensity of the blue light. However, as discussed above, at any instant in time, sensed red and blue light do not come from the same point on the ground. The red and blue light from a single point on the ground are sensed by the two detectors at different times. In the illustration in FIG. 1, the red detector sees a given point on the ground before the blue detector sees the same point. For example, the red detector sees point 52 when sensor 10 is at point 74. The blue detector sees point 52 when the sensor 10 is at point 80.

The distance between points 52 and 54 is the amount that the red and blue light are dispersed spatially by the atmosphere. A measurement of this distance gives an indication of the amount of dispersion introduced by the atmosphere. This measurement can be obtained by measuring the time between when the red detector sees point 52 and when the blue detector sees point 52 as the sensor 10 scans the ground. Since it is assumed that one knows the speed at which the ground is being scanned by the sensor 10, the time differential measured gives a measurement of the amount of dispersion.

Figure 2:
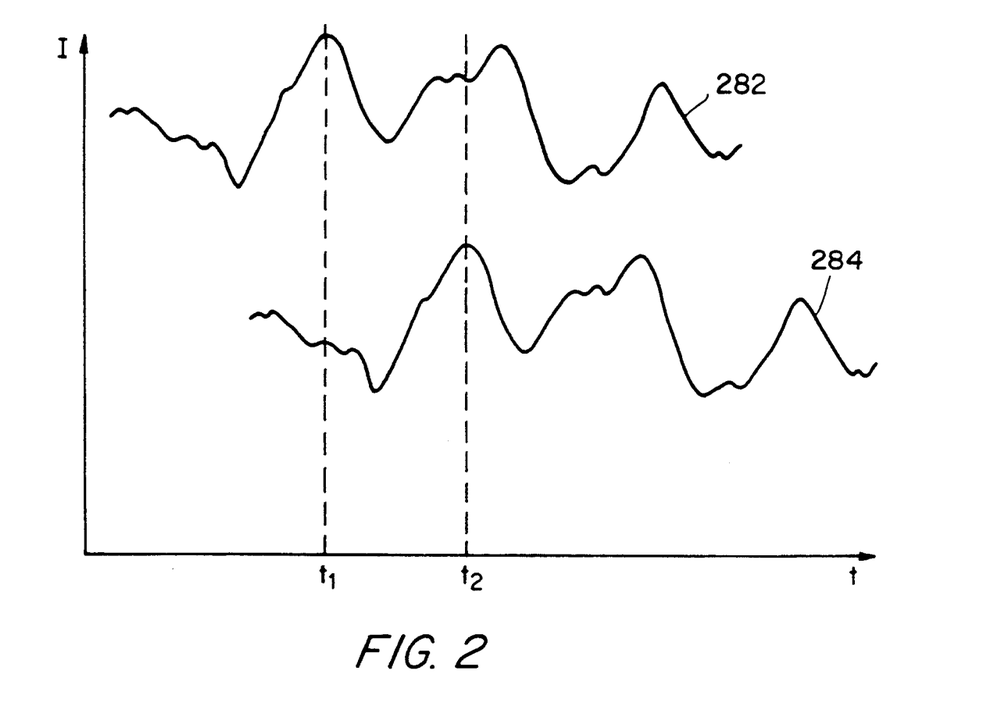
FIG. 2 is a schematic plot of detected intensity versus time for each of the first and second light detecting systems when the dispersion sensor scans a ground scene.

A ground scene will produce an optical detector signal based on the particular structure in the scene. This signal will be replicated but shifted in time at the different wavelengths as shown in FIG. 2. The signals will not be perfectly replicated due to additive noise in the detection process and a difference in spatial resolution with wavelength. It is the displacement in time between these two shifted signals at the two wavelengths that is measured to determine the atmospheric dispersion when viewing a ground scene.

FIG. 2 is a plot of detector output versus time for the sensor 10 as it scans a ground scene 12. Curve 282 illustrates the output of the red detector, and curve 284 is the blue detector output. A processing system receives and monitors the signals 282 and 284 from the red and blue detectors. The processing system compares the two signals and generates an output signal indicative of the relative time delay ($t_2 - t_1$) between the blue and red detector signals. Since the speed at which the sensor 10 scans the scene is known, this time duration is indicative of the amount of spectral dispersion introduced by the atmosphere.

The dispersion sensor can also be used when scanning the sky or space. In this application, detection of white light point sources such as stars by the different color detecting systems is used to measure dispersion.

Figure 3:
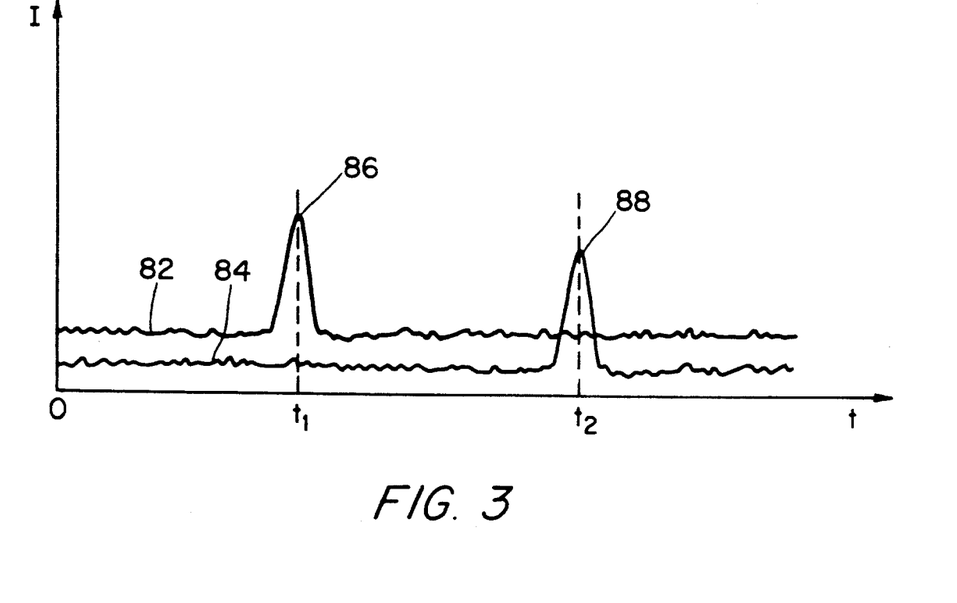
FIG. 3 is a schematic plot of detected intensity versus time for each of the first and second light detecting systems when the dispersion sensor scans the sky for point sources.

FIG. 3 is a simplified schematic illustration of the red and blue detecting system outputs versus time while the sensor 10 scans the sky. Curve 82 shows the intensity sensed by the red detector, and curve 84 shows the intensity sensed by the blue detector.

At time $t = 0$, the sensor is scanning the sky for point sources. The outputs of both the red and the blue detectors show essentially level ambient noise readings At time $t_1$, curve 82 shows a peak 86 in the red detector output. This indicates that the red detector detected a bright point source. At time $t_2$, the blue detector detects the same bright point source. This is indicated by the peak 88 at time $t_2$ in the blue detector curve 84. After time $t_2$ the sensor 10 returns to the ambient noise level. The processing system receives the signals 82 and 84 and computes the time delay between them to determine the atmospheric dispersion.

Figure 4:
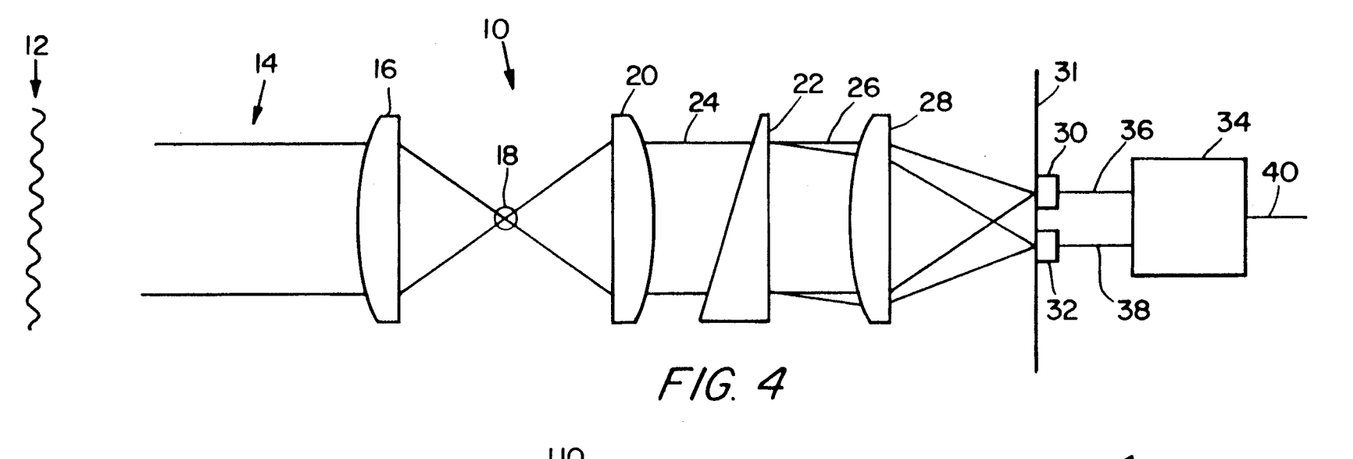
FIG. 4 schematically depicts an embodiment of the dispersion sensor of the present invention having a pinhole aperture and a prism.

FIG. 4 schematically depicts an embodiment of the dispersion sensor 10 of the present invention. Light 14 from a scene 12 impinges upon input lens 16. The input lens 16 focuses the light through a pinhole aperture 18. Light from the aperture 18 is directed to collimating lens 20. Collimated light 24 from lens 20 is directed to prism 22. It should be noted that a prism is utilized to show the concept, but a diffraction grating or other dispersion mechanism or mechanism for spectral separation can be utilized in place of the prism to perform the same function as the prism. The prism 22 spectrally disperses the light as shown at 26. Lens 28 focuses the dispersed light 26 onto the image plane 31. Thus, the image of the aperture 18 is a spectrum spatially distributed along the image plane 31.

Detectors 30 and 32 are positioned on the image plane 31 and are spaced in order to receive only two wavelength bands of the light entering the sensor. For example, detector 30 may be positioned to detect the red band of the spectrum while detector 32 is positioned to detect the blue band of the spectrum. Electrical signals 36 and 38 indicate the intensity of the light detected by detectors 30 and 32, respectively. These signals 36 and 38 are applied to processing circuit 34.

As previously described, the processing circuit 34 receives and monitors the detector output signals 36 and 38 and determines the time delay between them. Using the sensed time delay, a signal 40 indicative of the atmospheric dispersion is generated.

Figure 5:
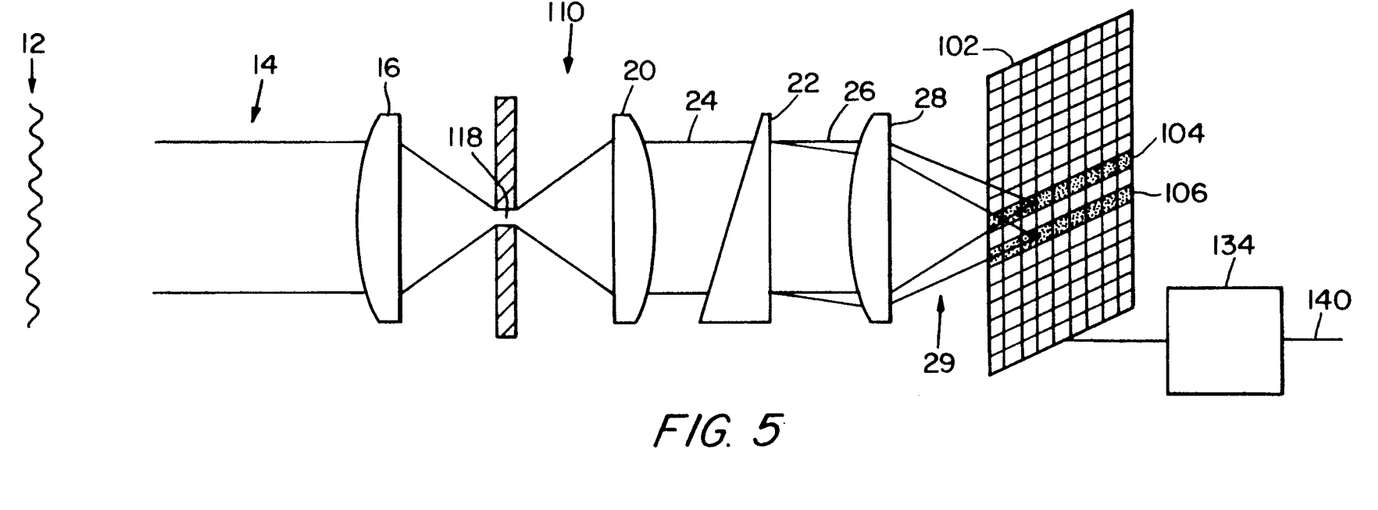
FIG. 5 schematically depicts an embodiment of the dispersion sensor of the present invention having a single-slit aperture and using an array of pixels to detect light.

FIG. 5 schematically depicts another embodiment 110 of the dispersion sensor. In this embodiment, the aperture is a single slit 118 rather than a pinhole. As shown in the FIGURE, the slit runs in and out of the page. Once again, the light from the aperture 118 is spectrally dispersed by the prism 22. The slit 118 is imaged as a spectrum spatially displaced along the image plane.

In this embodiment, the light focused on the image plane is detected by a two-dimensional array of pixels 102. The array of pixels 102 is oriented such that each row in the array senses a single wavelength band in the spectrum. It should be noted that the array 102 is shown in perspective to clarify the description. In actuality, the array 102 is oriented orthogonal to the page parallel to the slit 118.

In FIG. 5, two rows 104 and 106 of pixels are shown. Each of the rows detects a single wavelength band in the dispersed light on the image plane. For example, row 104 may detect the red light in the spectrum while 106 may detect the blue light.

Each pixel in the two-dimensional array 102 outputs an electrical signal which is indicative of the intensity of the light sensed by that pixel. The intensity signals of each pixel are read out of the array 102 and analyzed by processing circuit 134. In one embodiment, this analysis consists of summing up the intensity readings of each pixel in a row to obtain a total intensity value for each wavelength. This time varying total intensity signal of one wavelength is compared to the corresponding signal for the other wavelength. The signals are cross correlated, and the time delay between the two signals is computed. This time delay is used by the processing circuit 134 to generate signal 140. The signal 140 is indicative of the dispersion introduced by the atmosphere.

Figure 6:
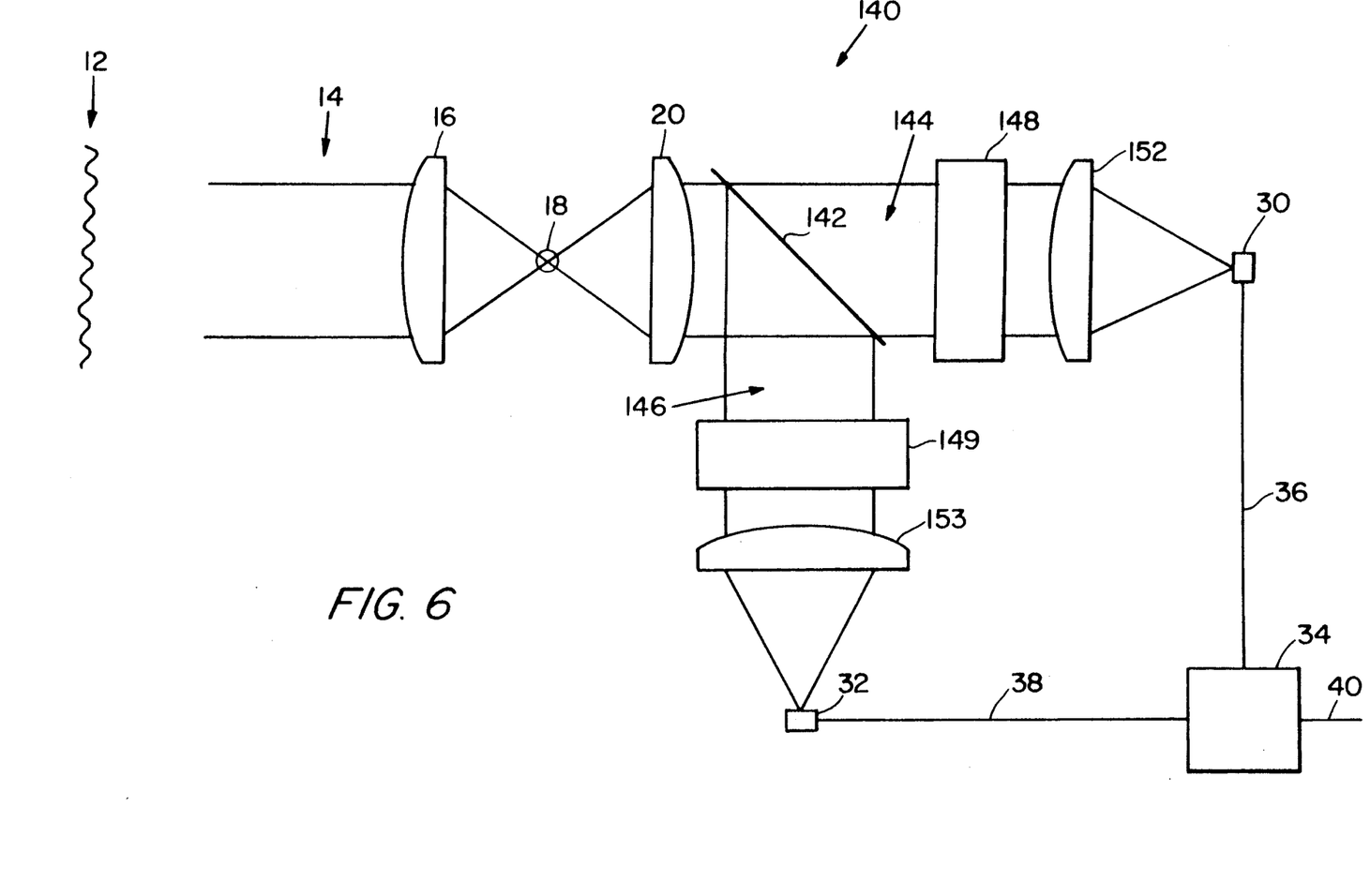
FIG. 6 schematically depicts an embodiment of the dispersion sensor of the present invention having a beam splitter and a pair of optical filters.

FIG. 6 depicts another embodiment 140 of the sensor. In this embodiment, the prism 22 of the previous embodiments is replaced with a beam splitter 142, either a dichroic beam splitter or a partially transmitting mirror. Light from the collimating lens 20 strikes the beam splitter 142. Some light 144 is transmitted to optical filter 148. The optical filter 148 blocks transmission of all light except light of the first wavelength band. That light is focused by lens 152 onto detector 30. The detector 30 outputs signal 36 to the processing circuit 34.

The remaining light 146 is reflected by the beam splitter 142 toward optical filter 149. The optical filter 149 blocks transmission of all light other than light of the second wavelength band. That light is transmitted to the focusing lens 153 which focuses the light on detector 32. The detector 32 outputs signal 38 to the processing circuit 34. The processing circuit 34 computes the time delay between the signals 36 and 38 and outputs signal 40 which is indicative of the atmospheric dispersion.

Figure 7:
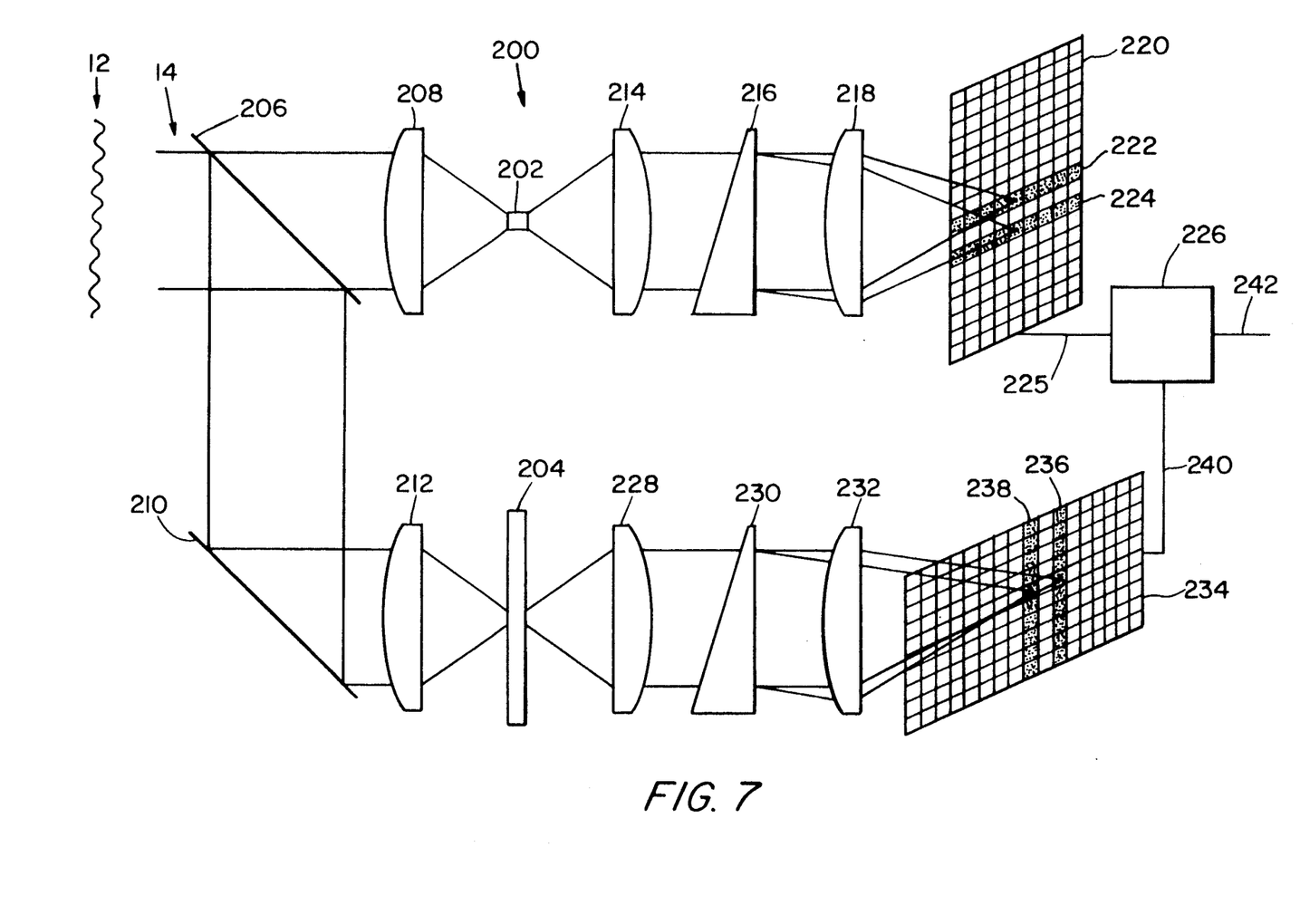
FIG. 7 schematically depicts an embodiment of the dispersion sensor of the present invention having orthogonal slits as an aperture.

The apertures in the dispersion sensors described to this point have been either pinholes or single slits. FIG. 7 shows an embodiment 200 of the dispersion sensor of the present invention in which the scan direction may be oriented arbitrarily with respect to the dispersion direction. In this embodiment, the aperture consists of a pair of substantially orthogonal slits 202 and 204. Light 14 from the scene 12 enters the system and is split by a partially reflecting mirror 206. Some of the light is transmitted to lens 208. The remainder of the light is reflected to mirror 210 and then to lens 212.

Lens 208 focuses light through the horizontal slit 202, oriented perpendicular to the page. Light leaving the slit 202 is collimated by lens 214. The light is dispersed by prism 216 and then focused by lens 218 onto a two-dimensional array 220 of pixels. It should be noted that the method of spectral separation can be any of the methods shown in FIGS. 4 through 6, and need not be a prism. As with the embodiment described in connection with FIG. 5, each row of pixels in the array 220 receives light from a single spectral band in the light. For example, row 222 may receive red light and row 224 may receive blue light. The pixel data of row 222 is read out of the array 220 as detection data for red light. Row 224 is read as detection data for blue light. This data is transmitted on signal line 225 to the processing circuit 226.

Lens 212 focuses light through the vertical slit 204. The light exiting the slit 204 impinges on lens 228. The lens 228 collimates the light and transmits it to prism 230 where it is spectrally dispersed. Lens 232 focuses the dispersed light onto a second two-dimensional array 234 of pixels.

Because the slit 204 is oriented orthogonal to the horizontal slit 202, the spectral image of the slit 204 is oriented orthogonal to the image of slit 202. Therefore, the array of pixels 234 is oriented orthogonal to the array 220. Each row of pixels in the array 234 detects light in a single spectral band. Row 236 receives light of a first wavelength band, for example, red light, while row 238 receives light of a second wavelength band, for example, blue light. Red light intensity data is read from row 236 of the array 234. Blue light data is read from row 238. The data is transmitted to the processing circuit 226 via the signal line 240.

The processing circuit 226 in this embodiment processes the two pairs of data signals. Specifically, the processing circuit 226 processes data for the red and blue light in the horizontal-slit array 220 and red and blue data for the vertical-slit array 234. The processing circuit 226 performs the time delay measurement between wavelength detections for both arrays 220 and 234.

Because of the orthogonal orientation between the slits 202 and 204, the detection and processing can be performed in any direction within the two-dimensional plane defined by the orthogonal slits. Each slit assembly measures the vector component of the atmospheric dispersion normal to the slit. The scan direction may be oriented arbitrarily with respect to the direction in which the atmosphere disperses light.

Figure 8:
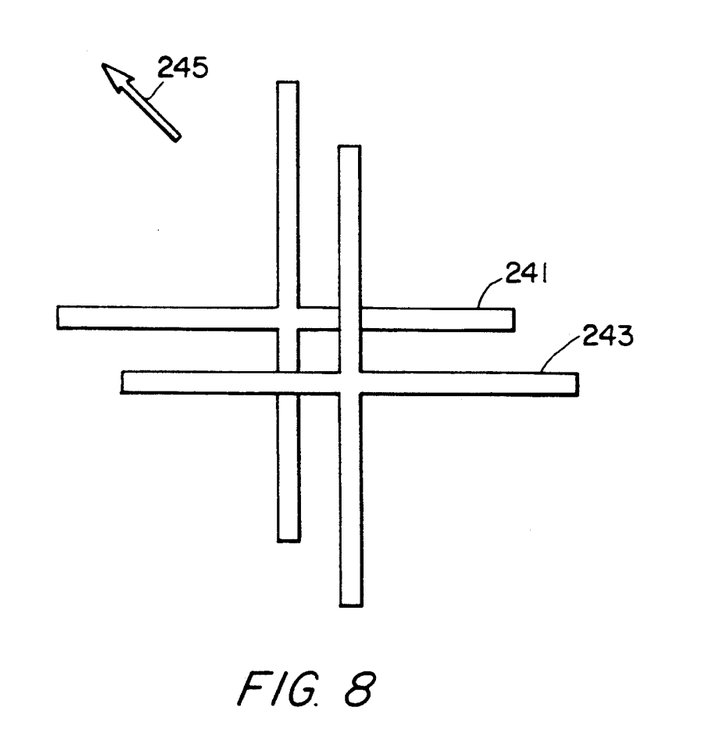
FIG. 8 schematically depicts the displacement of the footprints of the orthogonal slit aperture on the ground for two wavelength bands.

An image of the scene being viewed is formed upon the pair of orthogonal slits. The image which is formed upon the slits is sheared in color as a result of the atmospheric dispersion. Equivalently, referring to FIG. 8, the footprint of the slits as projected on the earth is sheared or displaced by color. The footprint 241 of the first spectral band is displaced from the footprint 243 of the second spectral band. Thus, as the scene is scanned across each slit in the arbitrary direction indicated by the arrow 245, there is a time delay as a function of wavelength between correlated signals from the scene. This time delay is a direct measure of the amount of atmospheric dispersion. This time delay is recovered by spectrally dispersing the light that passes through the slits. Accordingly, the slits are reimaged through the prism or other dispersive device to form a displaced image of the slit for each wavelength band of interest. The signal versus time for each band is cross-correlated against the other wavelength bands of interest. The relative time delay between the various signals is a direct measure of the vector components of the atmospheric dispersion since the scan rate is known and the scan direction relative to the slit orientation is known or can be deduced from the vector components.

Figure 9:
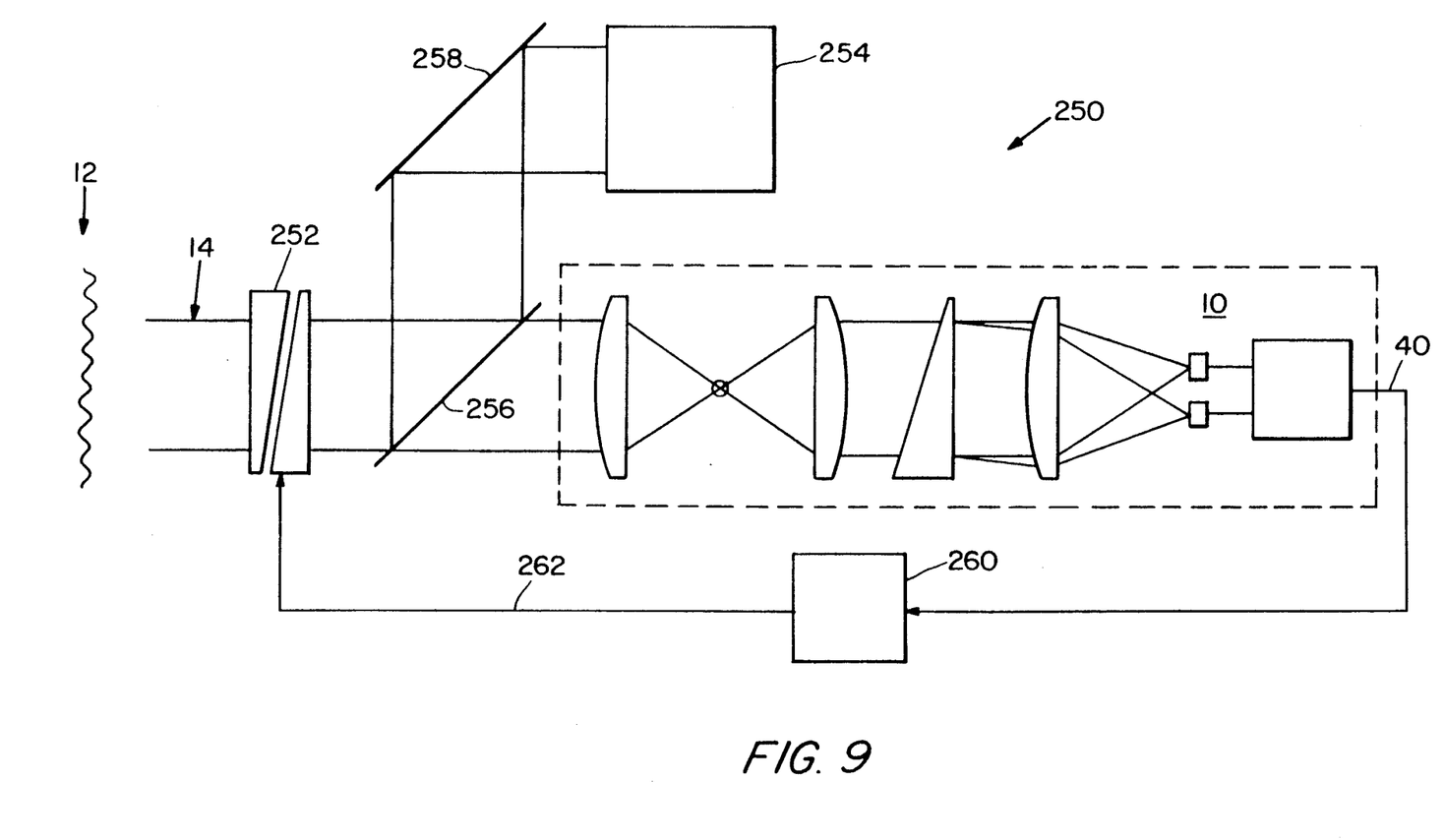
FIG. 9 schematically depicts an optical system using the dispersion sensor of the present invention.

FIG. 9 depicts a general optical system 250 which utilizes the dispersion sensor 10 of the present invention. The dispersion sensor 10 shown in the system 250 is the embodiment with the pinhole aperture and the pair of optical detectors. It will be understood that any of the embodiments of the sensor previously described herein are applicable to the following description of the overall optical system 250.

Light 14 from a scene 12 impinges upon Risley prism 252. The Risley prism 252 introduces an adjustable amount of spectral dispersion into the incoming light 14. The prism 252 is controllable to adjust the amount of dispersion. Light exiting the Risley prism 252 is directed to the subsequent optical components 254 in the optical system 250 as well as the dispersion sensor 10. In FIG. 9, the means of directing the light includes a partially reflecting mirror 256 and a completely reflecting mirror 258. It will be understood that other means of directing the light to the optical components 254 and the dispersion sensor 10 can be used.

Figure 10:
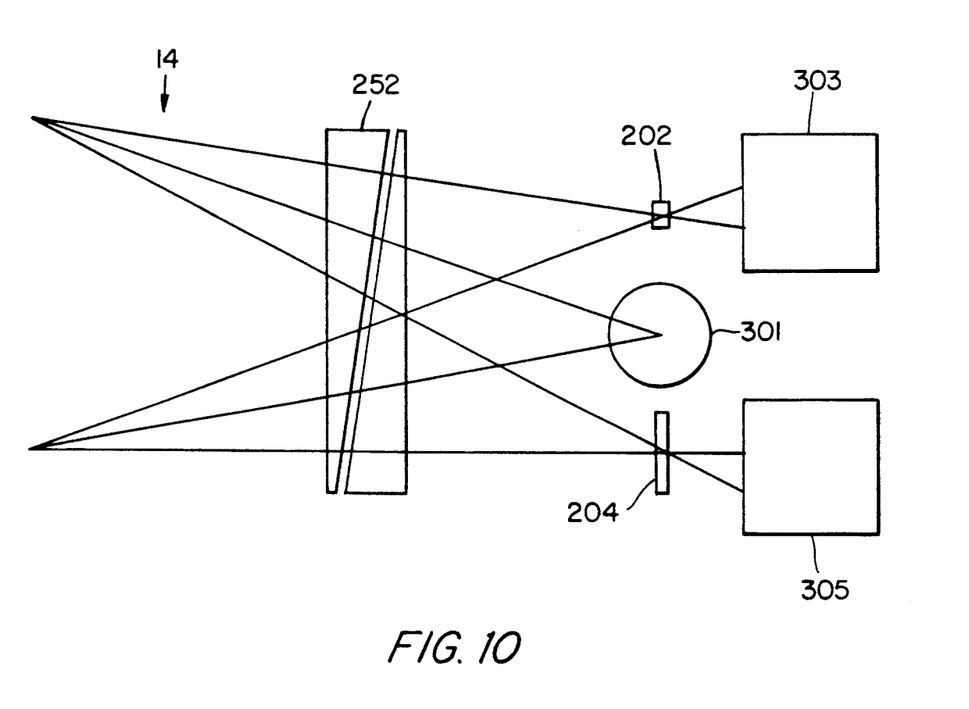
FIG. 10 schematically depicts an optical system employing the dispersion sensor of the present invention with the orthogonal slits of the aperture outside the desired field of view of the optical system.

For example, referring to FIG. 10, the slits 202, 204 of the dispersion sensor can be located outside of the field of view 301 of the optical system. In this embodiment, no partially transmitting optics or beam splitters are required to incorporate the dispersion sensor into the system. The dispersion sensor does not interfere with the field of view of the optical system. Light passes through the horizontal slit 202 to the horizontal-slit portion 303 of the dispersion sensor, and light passes to the verticalslit portion 305 through the vertical slit 204.

Referring again to FIG. 9, the light 14 from the scene 12 is scanned into the optical system 250 as previously described. The dispersion sensor 10 generates the atmospheric dispersion signal 40 and transmits it to a control circuit 260. While monitoring the signal 40, the control circuit 260 generates and transmits a control signal 262 to the Risley prism 252. The control signal 262 adjusts the Risley prism 252 to reduce the sensed net dispersion, as indicated by signal 40, to zero. This is obtained by adjusting the Risley prisms such that the relative time delay between the detector signals for the first and second wavelength bands is reduced to zero.

The Risley prism 252 is adjusted to compensate for the atmospheric dispersion by introducing its own dispersion into the incoming light 14. Therefore, the light which reaches optical components 254 in the system 250 has virtually no net spectral dispersion.

While this invention has been particularly shown and described with references to preferred embodiments thereof, it will be understood by those skilled in the art that various changes in form and details may be made therein without departing from the spirit and scope of the invention as defined by the appended claims.

The invention claimed is:

1. An optical dispersion sensor comprising:
   an aperture near the image plane of a scanning optical system for receiving light from a scene;

a first light detecting system for receiving the light from the aperture and detecting light of a first wavelength band in the light from the aperture, said first light detecting system generating signals corresponding to the detected light of the first wavelength band;

a second light detecting system for receiving the light from the aperture and detecting light of a second wavelength band in the light from the aperture, said second light detecting system generating signals corresponding to the detected light of the second wavelength band; and a processing circuit for receiving the signals from the first and second light detecting systems and sensing the time delay between the signals.

2. The optical dispersion sensor of claim 1 wherein the aperture is an approximately circular pinhole.

3. The optical dispersion sensor of claim 1 wherein the aperture is a single slit.

4. The optical dispersion sensor of claim 1 wherein the aperture is a pair of approximately orthogonal slits.

5. The optical dispersion sensor of claim 1 wherein the light detecting systems include a spectrometer.

6. The optical dispersion sensor of claim 1 wherein the light detecting systems comprise a dichroic beam splitter, said dichroic beam splitter directing light of the first wavelength band to an optical detector in the first light detecting system and directing light of the second wavelength band to an optical detector in the second light detecting system.

7. The optical dispersion sensor of claim 6 wherein:
the first light detecting system comprises an optical filter adapted to transmit only light of the first wavelength band; and
the second light detecting system comprises an optical filter adapted to transmit only light of the second wavelength band.

8. The optical dispersion sensor of claim 1 further comprising a partially transmitting mirror, said partially transmitting mirror directing some of the light from the aperture to the first light detecting system and directing some of the light from the aperture to the second light detecting system.

9. The optical dispersion sensor of claim 8 wherein:
the first light detecting system comprises an optical filter adapted to transmit only light of the first wavelength band; and
the second light detecting system comprises an optical filter adapted to transmit only light of the second wavelength band.

10. The optical dispersion sensor of claim 1 wherein each of the first and second light detecting systems comprises an array of pixels.

11. An optical system with compensation for atmospheric dispersive effects comprising:
an input opening for allowing light from a scene into the system;
an adjustable dispersive element coupled to the input opening for receiving the light from the scene and introducing spectral dispersion into the light, the amount of said spectral dispersion being adjustable;
an aperture near an image plane of the optical system for receiving light from the adjustable dispersive element;
a first light detecting system for receiving light from the aperture and detecting light of a first wavelength band in the light, said first light detecting system generating signals corresponding to the detected light of the first wavelength band;

a second light detecting system for receiving the light from the aperture and detecting light of a second wavelength band in the light, said second light detecting system generating signals corresponding to the detected light of the second wavelength band;

a processing circuit for receiving the signals from the first and second light detecting systems and sensing the relative time delay between the signals; and a control circuit for adjusting the spectral dispersion introduced by the adjustable dispersive element until the relative time delay sensed by the processing circuit is approximately zero.

12. The optical system of claim 11 wherein the adjustable dispersive element is a Risley prism.

13. The optical system of claim 11 wherein the aperture is an approximately circular pinhole.

14. The optical system of claim 11 wherein the aperture is a single slit.

15. The optical system of claim 11 wherein the aperture is a pair of approximately orthogonal slits.

16. The optical system of claim 11 wherein the light detecting systems include a spectrometer.

17. The optical system of claim 11 wherein the light detecting systems comprise a dichroic beam splitter, said dichroic beam splitter directing light of the first wavelength band to an optical detector in the first light detecting system and directing light of the second wavelength band to an optical detector in the second light detecting system.

18. The optical system of claim 17 wherein:
the first light detecting system comprises an optical filter adapted to transmit light of the first wavelength band; and
the second light detecting system comprises an optical filter adapted to transmit light of the second wavelength band.

19. The optical system of claim 11 further comprising a partially transmitting mirror, said partially transmitting mirror directing some of the light from the aperture to the first light detecting system and directing some of the light from the aperture to the second light detecting system.

20. The optical system of claim 19 wherein:
the first light detecting system comprises an optical filter adapted to transmit light of the first wavelength band; and
the second light detecting system comprises an optical filter adapted to transmit light of the second wavelength band.

21. The optical system of claim 11 wherein each of the first and second light detecting systems comprises an array of pixels.

22. A method of sensing optical dispersion comprising:
scanning light from a scene through an aperture near an image plane of an optical system;
detecting light of a first wavelength band in the light from the aperture;
generating signals corresponding to the detected light of the first wavelength band;
detecting light of a second wavelength band in the light from the aperture;
generating signals corresponding to the detected light of the second wavelength band; and processing the generated signals to determine the relative time delay between the signals.

23. The method of claim 22 wherein the aperture is an approximately circular pinhole.

24. The method of claim 22 wherein the aperture is a single slit.

25. The method of claim 22 wherein the aperture is a pair of approximately orthogonal slits.

26. The method of claim 22 wherein the light detecting systems include a spectrometer.

27. The method of claim 22 wherein each of the detecting steps comprises:
splitting the light from the aperture with a dichroic beam splitter;
directing some of the light from the dichroic beam splitter toward the first light detecting system; and
directing some of the light from the dichroic beam splitter toward the second light detecting system.

28. The method of claim 27 wherein:
the step of detecting light of a first wavelength band further comprises filtering the light such that only light of the first wavelength band is transmitted to the first light detecting system; and
the step of detecting light of a second wavelength band further comprises filtering the light such that only light of the second wavelength band is transmitted to the second light detecting system.

29. The method of claim 22 wherein each of the detecting steps comprises:
splitting the light from the aperture with a partially transmitting mirror;
directing some of the light from the partially transmitting mirror toward the first light detecting system; and
directing some of the light from the partially transmitting mirror toward the second light detecting system.

30. The method of claim 29 wherein:
the step of detecting light of a first wavelength band further comprises filtering the light such that only light of the first wavelength band is transmitted to the first light detecting system; and
the step of detecting light of a second wavelength band further comprises filtering the light such that only light of the second wavelength band is transmitted to the second light detecting system.

31. The method of claim 22 wherein each of the detecting steps comprises receiving light with an array of pixels.

32. A method of compensating for atmospheric optical dispersive effects in a scanning optical system comprising:
allowing light from a scene to be scanned into the scanning optical system;
introducing spectral dispersion into the light with an adjustable dispersive element, the amount of said spectral dispersion being adjustable;
passing light from the dispersive element through an aperture near an image plane of an optical system;
detecting light of a first wavelength band in the light from the aperture;
generating signals corresponding to the detected light of the first wavelength band;
detecting light of a second wavelength band in the light from the aperture;
generating signals corresponding to the detected light of the second wavelength band;
processing the generated signals to determine the relative time delay between the signals; and
adjusting the amount of spectral dispersion introduced by the adjustable dispersive element such that the time delay determined in the processing step is reduced to approximately zero.

33. The method of claim 32 wherein the adjustable dispersive element is a Risley prism.

34. The method of claim 32 wherein the aperture is an approximately circular pinhole.

35. The method of claim 32 wherein the aperture is a single slit.

36. The method of claim 32 wherein the aperture is a pair of approximately orthogonal slits.

37. The method of claim 32 wherein the optical system comprises a spectrometer.

38. The method of claim 32 wherein each of the detecting steps comprises:
splitting the light from the aperture with a dichroic beam splitter;
directing some of the light from the dichroic beam splitter toward the first light detecting system; and
directing some of the light from the dichroic beam splitter toward the second light detecting system.

39. The method of claim 38 wherein:
the step of detecting light of a first wavelength band further comprises filtering the light such that only light of the first wavelength band is transmitted to the first light detecting system; and
the step of detecting light of a second wavelength band further comprises filtering the light such that only light of the second wavelength band is transmitted to the second light detecting system.

40. The method of claim 32 wherein each of the detecting steps comprises:
splitting the light from the aperture with a partially transmitting mirror;
directing some of the light from the partially transmitting mirror toward the first light detecting system; and
directing some of the light from the partially transmitting mirror toward the second light detecting system.

41. The method of claim 40 wherein:
the step of detecting light of a first wavelength band further comprises filtering the light such that only light of the first wavelength band is transmitted to the first light detecting system; and
the step of detecting light of a second wavelength band further comprises filtering the light such that only light of the second wavelength band is transmitted to the second light detecting system.

42. The method of claim 32 wherein each of the detecting steps comprises receiving light with an array of pixels.

* * * * *